US010238722B2

(12) United States Patent
Shalgi et al.

(10) Patent No.: US 10,238,722 B2
(45) Date of Patent: Mar. 26, 2019

(54) PIGMENT EPITHELIUM DERIVED FACTOR (PEDF) FOR THE TREATMENT OF UTERINE FIBROIDS

(71) Applicant: Ramot at Tel-Aviv University Ltd., Tel-Aviv (IL)

(72) Inventors: Ruth Shalgi, Herzlia (IL); Dana Chuderland, Ramat-HaSharon (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 0 days.

(21) Appl. No.: 15/525,062

(22) PCT Filed: Nov. 24, 2015

(86) PCT No.: PCT/IL2015/051132
§ 371 (c)(1),
(2) Date: May 7, 2017

(87) PCT Pub. No.: WO2016/084070
PCT Pub. Date: Jun. 2, 2016

(65) Prior Publication Data
US 2018/0043001 A1 Feb. 15, 2018

Related U.S. Application Data

(60) Provisional application No. 62/083,356, filed on Nov. 24, 2014.

(51) Int. Cl.
*A61K 38/18* (2006.01)
*A61P 15/00* (2006.01)
*A61K 38/57* (2006.01)
*A61K 9/00* (2006.01)

(52) U.S. Cl.
CPC .......... *A61K 38/57* (2013.01); *A61K 9/0019* (2013.01); *A61K 9/0034* (2013.01); *A61K 38/18* (2013.01)

(58) Field of Classification Search
None
See application file for complete search history.

(56) References Cited

U.S. PATENT DOCUMENTS

| | | |
|---|---|---|
| 2003/0064917 A1 | 4/2003 | Crawford et al. |
| 2003/0216286 A1 | 11/2003 | Bouck et al. |
| 2004/0071659 A1 | 4/2004 | Chang et al. |
| 2007/0087967 A1 | 4/2007 | Bouck et al. |
| 2009/0118191 A1 | 5/2009 | Volz et al. |
| 2009/0192130 A1 | 7/2009 | Nieman et al. |
| 2013/0053312 A1 | 2/2013 | Shalgi et al. |
| 2014/0271612 A1 | 9/2014 | Leppert et al. |

FOREIGN PATENT DOCUMENTS

| | | | |
|---|---|---|---|
| WO | WO-0162725 A2 * | 8/2001 | ............ A61K 38/57 |
| WO | WO 2011/058557 | 5/2011 | |
| WO | WO 2016/084070 | 6/2016 | |

OTHER PUBLICATIONS

Tal et al., "The role of angiogenic factors in fibroid pathogenesis: potential implications for future therapy," Human Reproduction Update 20:194-216 (available online Sep. 29, 2013).*
Wallach et al., "Uterine Myomas: An Overview of Development, Clinical Features, and Management," Obstet. Gynecol. 104:393-406 (2004).*
International Preliminary Report on Patentability dated Jun. 8, 2017 From the International Bureau of WIPO Re. Application No. PCT/IL2015/051132. (9 Pages).
International Search Report and the Written Opinion dated Feb. 21, 2016 From the International Searching Authority Re. Application No. PCT/IL2015/051132.
Chabbert-Buffet et al. "Fibroid Growth and Medical Options for Treatment", Fertility and Sterility, 102(3): 630-639, Sep. 2, 2014. Abstract, Table 1, p. 633, Last Para—p. 635, Right Col., First Para, p. 636, 2nd Para.
Cheung et al. "Pigment Epithelium-Derived Factor Is Estrogen Sensitive and Inhibits the Growth of Human Ovarian Cancer and Ovarian Surface Epithelial Cells", Endocrinology, 147(9): 4179-4191, Published Online Jun. 15, 2006.
Chuderland et al. "Hormonal Regulation of Pigment Epithelium-Derived Factor (PEDF) Expression in the Endometrium", Molecular and Cellular Endocrinology, 390: 85-92, 2014.
Chuderland et al. "Hormonal Regulation of Pigment Epithelium-Derived Factor (PEDF) in Granulosa Cells", Molecular Human Reproduction, 19(2): 72-81, Published Online Oct. 16, 2012.
Chuderland et al. "Role of Pigment Epithelium-Derived Factor in the Reproductive System", Reproduction, 148(4): R53-R61, Published Online Jul. 21, 2014. Abstract, P.R58, Last Para.
Chuderland et al. "The Role of Pigment Epithelium-Derived Factor in the Pathophysiology and Treatment of Ovarian Hyperstimulation Syndrome in Mice", The Journal of Clinical Endocrinology and Metabolism, 98(2): E258-E266, Published Online Jan. 7, 2013.
Folkman "Angiogenesis: An Organizing Principles for Drug Discovery?", Nature Reviews Drug Discovery, 6: 273-286, Apr. 2007.
Islam et al. "Uterine Leiomyoma: Available Medical Treatments and New Possible Therapeutic Options", The Journal of Clinical Endocrinology & Metabolism, 98(3): 921-934, Published Online Feb. 7, 2013. Figs.2, 3, Table 1.
Jia et al. "Thrombospondin-1 and Pigment Epithelium-Derived Factor Enhance Responsiveness of KM12 Colon Tumor to Metronomic Cyclophosphamide But Have Disparate Effects on Tumor Metastasis", Cancer Letters, 330(2): 241-249, 2013.
Ma et al. "Combination of Anti-Angiogenesis With Chemotherapy for More Effective Cancer Treatment", Molecular Cancer Therapy, 7(12): 3670-3684, Dec. 2008.

(Continued)

*Primary Examiner* — Julie Ha
*Assistant Examiner* — Kristina M Hellman (57) ABSTRACT

A method of treating uterine fibroid in a subject in need thereof is provided. The method comprising administering to the subject a therapeutically effective amount of pigment epithelium-derived factor (PEDF), thereby treating the uterine fibroid in the subject.

19 Claims, 4 Drawing Sheets
Specification includes a Sequence Listing.

(56) References Cited

OTHER PUBLICATIONS

Manalo et al. "Pigment Epithelium-Derived Factor as An Anticancer Drug and New Treatment Methods Following the Discovery of Its Receptors: A Patent Perspective", Expert Opinion on Therapeutic Patents, 21(2): 121-130, Published Online Jan. 5, 2011.
Martini et al. "Inflammatory Fibroid Polyp of the Gallbladder Bearing A Platelet-Derived Growth Factor Receptor Alpha Mutation", Archives of Pathology & Laboratory Medicine, 137(5): 721-724, May 2013.
Nelius et al. Effect of PEDF on the In Vivo Antitumor Activities of Low-Dose Chemotherapy in CRPC, 2013 Genitourinary Cancers Sympsoium, General Poster Session A: Prostate Cancer, Journal of Clinical Oncology, 31(Suppl.6): # 173, 2013.
Palmieri et al. "Age-Related Expression of PEDF/EPC-1 in Human Endometrial Stromal Fibroblasts: Implications for Interactive Senescence", Experimental Cell Research, 247(1): 142-147, Feb. 25, 1999.
Pollina et al. "Regulating the Angiogenic Balance in Tissues. A Potential Role for the Proliferative State of Fibroblasts", Cell Cycle, 7(13): 2056-2070, Jul. 1, 2008.
Simon "Introduction: Are We Advancing in Our Scientific Understanding and Therapeutic Improvement of Uterine Fibroids . . . or Not?", Fertility and Sterility, 102(3): 611-612, Sep. 2, 2014. p. 611, First Para, p. 612, Left Col., 2nd Para, 3rd Para, Last Para.
Tal et al. "The Role of Angiogenic Factors in Fibroid Pathogenesis: Potential Implications for Future Therapy", Human Reproduction Update, 20(2): 194-216, Advanced Access Sep. 29, 2013. Abstract.
Yamagishi et al. "Pigment Epithelium-Derived Factor (PEDF) Blocks Angiotensin II Signaling in Endothelial Cells Via Suppression of NADPH Oxidase: A Novel Anti-Oxidative Mechanism of PEDF", Cell and Tissue Research, 320(3): 437-445, Published Online Apr. 22, 2005.
Supplementary European Search Report and the European Search Opinion dated Oct. 4, 2018 From the European Patent Office Re. Application No. 15864173.8. (5 Pages).

\* cited by examiner

| | volume(mm3) measured by: | | | | | weight(mg) |
|---|---|---|---|---|---|---|
| | US | | | | caliper | |
| | 8 days | 13 days | 22 days | 28 days | 29 days | 29 days |
| mouse1 | undetectable | undetectable | undetectable | 3.6 | 10.6 | 26 |
| mouse2 | undetectable | undetectable | undetectable | 18.7 | 27.2 | 93 |

Figure 5C
rPEDF Control

Figure 5B
Weight

Figure 5A
Volume

SEQUENCE LISTING

```
<160> NUMBER OF SEQ ID NOS: 13

<210> SEQ ID NO 1
<211> LENGTH: 1490
<212> TYPE: DNA
<213> ORGANISM: Homo sapiens

<400> SEQUENCE: 1
ggacgctgga ttagaaggca gcaaaaaaag atctgtgctg gctggagccc cctcagtgtg      60
caggcttaga gggactaggc tgggtgtgga gctgcagcgt atccacaggc cccaggatgc     120
aggccctggt gctactcctc tgcattggag ccctcctcgg gcacagcagc tgccagaacc     180
ctgccagccc cccggaggag ggctcccag accccgacag cacaggggcg ctggtggagg     240
aggaggatcc tttcttcaaa gtccccgtga acaagctggc agcggctgtc tccaacttcg     300
```

```
gctatgacct gtaccgggtg cgatccagca tgagccccac gaccaacgtg ctcctgtctc      360
ctctcagtgt ggccacggcc ctctcggccc tctcgctggg agcggacgag cgaacagaat      420
ccatcattca ccgggctctc tactatgact tgatcagcag cccagacatc catggtacct      480
ataaggagct ccttgacacg gtcactgccc cccagaagaa cctcaagagt gcctcccgga      540
tcgtctttga gaagaagctr cgcataaaat ccagctttgt ggcacctctg gaaaagtcat      600
atgggaccag gcccagagtc ctgacgggca accctcgctt ggacctgcaa gagatcaaca      660
actgggtgca ggcgcagatg aaagggaagc tcgccaggtc cacaaaggaa attcccgatg      720
agatcagcat tctccttctc ggtgtggcgc acttcaaggg gcagtgggta caaagtttg      780 actccagaaa gacttccctc gaggatttct acttggatga agagaggacc gtgagggtcc      840
ccatgatgtc ggaccctaag gctgttttac gctatggctt ggattcagat ctcagctgca      900
agattgccca gctgcccttg accggaagca tgagtatcat cttcttcctg cccctgaaag      960
tgacccagaa tttgaccttg atagaggaga gcctcacctc cgagttcatt catgacatag     1020
accgagaact gaagaccgtg caggcggtcc tcactgtccc caagctgaag ctgagttacg     1080
aaggcgaagt caccaagtcc ctgcaggaga tgaagctgca atccttgttt gattcaccag     1140
actttagcaa gatcacaggc aaacccatca agctgactca ggtggaacac cgggctggct     1200
ttgagtggaa cgaggatggg gcgggaacca ccccagccc agggctgcag cctgcccacc      1260
tcaccttccc gctggactat caccttaacc agcctttcat cttcgtactg agggacacag     1320
acacaggggc ccttctcttc attggcaaga ttctggaccc caggggcccc taatatccca     1380
gtttaatatt ccaataccct agaagaaaac ccgagggaca gcagattcca caggacgga     1440 aggctgcccc tgtaaggttt caatgcatac aataaaagag ctttatccct                1490

<210> SEQ ID NO 2
<211> LENGTH: 1552
<212> TYPE: DNA
<213> ORGANISM: Homo sapiens

<400> SEQUENCE: 2
ggtcgcttta agaaaggagt agctgtaatc tgaagcctgc tggacgctgg attagaaggc       60
agcaaaaaaa gctctgtgct ggctggagcc ccctcagtgt gcaggcttag agggactagg      120
ctgggtgtgg agctgcagcg tatccacagg ccccaggatg caggccctgg tgctactcct      180
ctgcattgga gccctcctcg ggcacagcag ctgccagaac cctgccagcc cccggagga      240 gggctcccca gaccccgaca gcacaggggc gctggtggag gaggaggatc ctttcttcaa      300
agtccccgtg aacaagctgg cagcggctgt ctccaacttc ggctatgacc tgtaccgggt      360
gcgatccagc acgagcccca cgaccaacgt gctcctgtct cctctcagtg tggccacggc      420
cctctcggcc ctctcgctgg gagcggagca gcgaacagaa tccatcattc accgggctct      480
ctactatgac ttgatcagca gcccagacat ccatggtacc tataaggagc tccttgacac      540
ggtcactgcc cccagaagaa acctcaagag tgcctcccgg atcgtctttg agaagaagct     600
gcgcataaaa tccagctttg tggcacctct ggaaaagtca tatgggacca gcccagagt      660 cctgacgggc aaccctcgct tggacctgca agagatcaac aactgggtgc aggcgcagat      720
gaaagggaag ctcgccaggt ccacaaagga aattcccgat gagatcagca ttctccttct      780
cggtgtggcg cacttcaagg ggcagtgggt aacaaagttt gactccagaa agacttccct      840
cgaggatttc tacttggatg aagagaggac cgtgagggtc cccatgatgt cggaccctaa      900
```

-continued

```
ggctgtttta cgctatggct tggattcaga tctcagctgc aagattgccc agctgccctt      960
gaccggaagc atgagtatca tcttcttcct gcccctgaaa gtgacccaga atttgacctt     1020
gatagaggag agcctcacct ccgagttcat tcatgacata gaccgagaac tgaagaccgt     1080
gcaggcggtc ctcactgtcc ccaagctgaa gctgagttat gaaggcgaag tcaccaagtc     1140
cctgcaggag atgaagctgc aatccttgtt tgattcacca gactttagca agatcacagg     1200
caaacccatc aagctgactc aggtggaaca ccgggctggc tttgagtgga acgaggatgg     1260
ggcgggaacc accccagcc cagggctgca gcctgcccac ctcaccttcc cgctggacta     1320
tcaccttaac cagcctttca tcttcgtact gagggacaca gacacagggg cccttctctt     1380
cattggcaag attctggacc ccaggggccc ctaatatccc agtttaatat tccaatacccc     1440 tagaagaaaa cccgagggac agcagattcc acaggcacg aaggctgccc ctgtaaggtt     1500
tcaatgcata caataaaaga gctttatccc taaaaaaaaa aaaaaaaaaa aa             1552
```

<210> SEQ ID NO 3
<211> LENGTH: 418
<212> TYPE: PRT
<213> ORGANISM: Homo sapiens

<400> SEQUENCE: 3

```
Met Gln Ala Leu Val Leu Leu Cys Ile Gly Ala Leu Leu Gly His
1               5                   10                  15

Ser Ser Cys Gln Asn Pro Ala Ser Pro Glu Glu Gly Ser Pro Asp
                20                  25                  30

Pro Asp Ser Thr Gly Ala Leu Val Glu Glu Asp Pro Phe Phe Lys
                35                  40                  45

Val Pro Val Asn Lys Leu Ala Ala Val Ser Asn Phe Gly Tyr Asp
50                  55                  60

Leu Tyr Arg Val Arg Ser Ser Thr Ser Pro Thr Thr Asn Val Leu Leu
65                  70                  75                  80

Ser Pro Leu Ser Val Ala Thr Ala Leu Ser Ala Leu Ser Leu Gly Ala
                85                  90                  95

Glu Gln Arg Thr Glu Ser Ile Ile His Arg Ala Leu Tyr Tyr Asp Leu
                100                 105                 110

Ile Ser Ser Pro Asp Ile His Gly Thr Tyr Lys Glu Leu Leu Asp Thr
                115                 120                 125

Val Thr Ala Pro Gln Lys Asn Leu Lys Ser Ala Ser Arg Ile Val Phe
                130                 135                 140

Glu Lys Lys Leu Arg Ile Lys Ser Ser Phe Val Ala Pro Leu Glu Lys
145                 150                 155                 160

Ser Tyr Gly Thr Arg Pro Arg Val Leu Thr Gly Asn Pro Arg Leu Asp
                165                 170                 175

Leu Gln Glu Ile Asn Asn Trp Val Gln Ala Gln Met Lys Gly Lys Leu
                180                 185                 190

Ala Arg Ser Thr Lys Glu Ile Pro Asp Glu Ile Ser Ile Leu Leu Leu
                195                 200                 205

Gly Val Ala His Phe Lys Gly Gln Trp Val Thr Lys Phe Asp Ser Arg
                210                 215                 220

Lys Thr Ser Leu Glu Asp Phe Tyr Leu Asp Glu Arg Thr Val Arg
225                 230                 235                 240

Val Pro Met Met Ser Asp Pro Lys Ala Val Leu Arg Tyr Gly Leu Asp
                245                 250                 255

Ser Asp Leu Ser Cys Lys Ile Ala Gln Leu Pro Leu Thr Gly Ser Met
```

```
            260                 265                 270
Ser Ile Ile Phe Phe Leu Pro Leu Lys Val Thr Gln Asn Leu Thr Leu
        275                 280                 285

Ile Glu Glu Ser Leu Thr Ser Glu Phe Ile His Asp Ile Asp Arg Glu
    290                 295                 300

Leu Lys Thr Val Gln Ala Val Leu Thr Val Pro Lys Leu Lys Leu Ser
305                 310                 315                 320

Tyr Glu Gly Glu Val Thr Lys Ser Leu Gln Glu Met Lys Leu Gln Ser
                325                 330                 335

Leu Phe Asp Ser Pro Asp Phe Ser Lys Ile Thr Gly Lys Pro Ile Lys
            340                 345                 350

Leu Thr Gln Val Glu His Arg Ala Gly Phe Glu Trp Asn Glu Asp Gly
        355                 360                 365

Ala Gly Thr Thr Pro Ser Pro Gly Leu Gln Pro Ala His Leu Thr Phe
    370                 375                 380

Pro Leu Asp Tyr His Leu Asn Gln Pro Phe Ile Phe Val Leu Arg Asp
385                 390                 395                 400

Thr Asp Thr Gly Ala Leu Leu Phe Ile Gly Lys Ile Leu Asp Pro Arg
                405                 410                 415

Gly Pro

<210> SEQ ID NO 4
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 4
gtgaaggtcg gtgtgaacgg                                           20

<210> SEQ ID NO 5
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 5
gtgatggcat ggactgtggt c                                         21

<210> SEQ ID NO 6
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 6
tgtggcctca ttcctcctac                                           20

<210> SEQ ID NO 7
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 7
tgagaatggg gacactgtga                                           20
```

```
<210> SEQ ID NO 8
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 8
ttgccattga gaaccctg                                                 18

<210> SEQ ID NO 9
<211> LENGTH: 18
<212> TYPE: DNA
<213> ORGANISM: Artificial sequence
<220> FEATURE:
<223> OTHER INFORMATION: Single strand DNA oligonucleotide

<400> SEQUENCE: 9
tgggatggca atgtccac                                                 18

<210> SEQ ID NO 10
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 10
ctcatggact gattatggac agga                                          24

<210> SEQ ID NO 11
<211> LENGTH: 25
<212> TYPE: DNA
<213> ORGANISM: Artificial sequence
<220> FEATURE:
<223> OTHER INFORMATION: Single strand DNA oligonucleotide

<400> SEQUENCE: 11
gcaggtcagc aaagaactta tagcc                                         25

<210> SEQ ID NO 12
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 12
ctatgcagat catgcggatc a                                             21

<210> SEQ ID NO 13
<211> LENGTH: 22
<212> TYPE: DNA
<213> ORGANISM: Artificial sequence
<220> FEATURE:
<223> OTHER INFORMATION: Single strand DNA oligonucleotide

<400> SEQUENCE: 13
tatgctgcag gaagctcatc tc                                            22
```

PIGMENT EPITHELIUM DERIVED FACTOR (PEDF) FOR THE TREATMENT OF UTERINE FIBROIDS

RELATED APPLICATIONS

This application is a National Phase of PCT Patent Application No. PCT/IL2015/051132 having International filing date of Nov. 24, 2015, which claims the benefit of priority under 35 USC § 119(e) of U.S. Provisional Patent Application No. 62/083,356 filed on Nov. 24, 2014. The contents of the above applications are all incorporated by reference as if fully set forth herein in their entirety.

SEQUENCE LISTING STATEMENT

The ASCII file, entitled 69779SequenceListing.txt, created on May 7, 2017, comprising 10,136 bytes, submitted concurrently with the filing of this application is incorporated herein by reference.

FIELD AND BACKGROUND OF THE INVENTION

The present invention, in some embodiments thereof, relates to Pigment epithelium-derived factor (PEDF) and uses of same in the treatment of uterine fibroids.

Uterine fibroids (leiomyomas) are the most common benign tumors in women. Fibroids disrupt the function of the uterus and cause excessive uterine bleeding, anemia, infertility, defective implantation of embryos, recurrent pregnancy loss, preterm labor, obstruction of labor, pelvic discomfort and urinary incontinence; in fact, uterine fibroids may mimic or mask malignant tumors. Approximately 200,000 hysterectomies, 30,000 myomectomies, and thousands of selective uterine-artery embolizations and high-intensity focused ultrasound procedures are performed annually in the United States to remove uterine fibroids. The annual economic burden of these tumors is estimated to be between 5.9 and 34.4 billion US $.

Uterine fibroids arise from the uterine smooth-muscle tissue (i.e., the myometrium). Histologically, fibroids are benign neoplasms composed of disordered smooth-muscle cells buried in abundant quantities of extracellular matrix. A striking feature of uterine fibroids is their dependency on the ovarian steroids estrogen and progesterone. Ovarian activity is essential for fibroid growth; most fibroids shrink after menopause. Gonadotropin-releasing-hormone (GnRH) analogues, which suppress ovarian activity and reduce circulating levels of estrogen and progesterone, shrink fibroids and reduce associated uterine bleeding.

Fibroids comprise a unique vascular architecture that consists of an avascular core surrounded by a well-vascularized myometrium caused, most likely, due to an angiogenic imbalance. Researchers suggest that the preliminary tumor, which is small in size with a minimal intrinsic blood supply, may release angiogenic factors as vascular endothelial growth factor (VEGF) that lead to an increase in the vascular density of the surrounding myometrium. This may, in turn, give rise to capillary sprouts that vascularize the small fibroid, promoting its growth and enlargement. This increase in vascular density of myometrium may account for the symptoms of menorrhagia observed in women with fibroids.

Pigment epithelium-derived factor (PEDF) is a non-inhibitory member of the serine protease inhibitors (serpin) superfamily, which was first described as a neurotrophic factor, able to promote and support the growth of neuronal cells. It was later found that on top of having neurotrophic activity, PEDF has an anti-angiogenic, anti-inflammatory and anti-oxidative properties. To date, two distinct PEDF receptors were proposed: an 80 kDa PEDF putative receptor (PEDF-$R^N$; PNPLA2) involved in PEDF neuroprotecting, pro-survival functions; and a 60 kDa PEDF putative receptor (PEDF-$R^A$; Laminin receptor) involved in PEDF pro-apoptotic, anti-angiogenic activities [Manalo et al. Expert Opin Ther Pat (2011): 21, 121-130; and Yamagishi et al. Cell Tissue Res (2005) 320: 437-445].

Although originally discovered in culture media of retinal pigment epithelial cells, PEDF is widely expressed throughout the body: the nervous system, ovary, uterine, liver and plasma. Despite the significant expression of PEDF in the reproductive system, there is only limited data about its function in the ovary and uterus [Cheung et al., Endocrinology, 2006. 147(9): p. 4179-91; Chuderland et al. J Clin Endocrinol Metab (2013) 98: E258-266; and Chuderland et al. Mol Hum Reprod (2013) 19: 72-81; Pollina et al., Cell Cycle, 2008. 7(13): p. 2056-70; Palmieri et al. Exp Cell Res, 1999. 247(1): p. 142-7.]. Previous work has suggested using PEDF in the treatment of tumors [Manalo et al. Expert Opin Ther Pat (2011): 21, 121-130] as well as in endometriosis (US20130053312).

Additional Related Background Art:
U.S. Patent Publication Number US20030216286;
U.S. Patent Publication Number US20070087967;
U.S. Patent Publication Number US20040071659;
U.S. Patent Publication Number US20090118191;
Nelius et al. [J Clin Oncol 31, 2013 (suppl 6; abstr 173)];
Ma and Waxman [Mol Cancer Ther. (2008) 7(12): 3670-3684];
Jia and Waxman [Cancer Lett. (2013) 330(2):241-9];
Chuderland et al. 2014 Mol. Cell. Endocrinol. 390:85-92;
Folkman et al. Nat. Rev. 6:273-286 (2007).

SUMMARY OF THE INVENTION

According to an aspect of some embodiments of the present invention there is provided a method of treating uterine fibroid in a subject in need thereof, the method comprising administering to the subject a therapeutically effective amount of pigment epithelium-derived factor (PEDF), thereby treating the uterine fibroid in the subject.

According to an aspect of some embodiments of the present invention there is provided a composition comprising pigment epithelium-derived factor (PEDF) for use in the treatment of uterine fibroid in a subject in need thereof.

According to an aspect of some embodiments of the present invention there is provided use of pigment epithelium-derived factor (PEDF) in the manufacture of a medicament identified for the treatment of uterine fibroid in a subject in need thereof.

According to some embodiments of the invention, the PEDF is attached to an intrauterine device.

According to some embodiments of the invention, the uterine fibroid comprises a plurality of fibroids.

According to some embodiments of the invention, the subject is not inflicted with cancer.

According to some embodiments of the invention, the subject is not inflicted with uterine fibroid associated infertility.

According to some embodiments of the invention, the subject is not diagnosed with infertility.

According to some embodiments of the invention, the subject is 55 years of age or younger.

According to some embodiments of the invention, the subject is 50 years of age or younger.

According to some embodiments of the invention, the subject is fertile.

According to some embodiments of the invention, the subject is 35-55 years of age.

According to some embodiments of the invention, the subject is 35-50 years of age.

According to some embodiments of the invention, the uterine fibroid is an intramural fibroid.

According to some embodiments of the invention, the uterine fibroid is a subserosal fibroid.

According to some embodiments of the invention, the uterine fibroid is a cervical fibroid.

According to some embodiments of the invention, the uterine fibroid is not a submucosal fibroid.

According to some embodiments of the invention, the PEDF is formulated local administration.

According to some embodiments of the invention, the local administration is by injection into the uterine fibroid.

According to some embodiments of the invention, the local administration is by an intrauteral device (IUD)-attached PEDF.

According to some embodiments of the invention, the PEDF is formulated systemic administration.

According to some embodiments of the invention, the local administration is by subcutaneous or intramuscular administration.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-B demonstrate the expression of PEDF receptors in Eker rat uterine leiomyoma ELT-3 cells.

FIG. 2 is a graph demonstrating that PEDF activates ERK phosphorylation in ELT-3 cells. ELT-3 cells were serum starved and then treated with rPEDF (1 or 100 nM) or Tris (Control) for the indicated periods of times. The y-axis represents phosphorylated ERK levels relative to general ERK, as evaluated by Western blot analysis.

FIGS. 4A-C show the in-vivo uterine fibroids mouse model used.

FIGS. 5A-C demonstrate the in-vivo therapeutic effect of rPEDF on uterine fibroids. Mice treated according to the setting depicted in FIG. 4A were treated with rPEDF (10 mg/kg; n=4) or Tris (control; n=2) once every 3 days from day 0 onwards.

DESCRIPTION OF SPECIFIC EMBODIMENTS OF THE INVENTION

The present invention, in some embodiments thereof, relates to compositions comprising pigment epithelium-derived factor (PEDF) and uses of same in the treatment of uterine fibroids.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Uterine fibroids (leiomyomas) are the most common benign tumors in women. Fibroids disrupt the function of the uterus and cause excessive uterine bleeding, anemia, infertility, defective implantation of embryos, recurrent pregnancy loss, preterm labor, obstruction of labor, pelvic discomfort and urinary incontinence; in fact, uterine fibroids may mimic or mask malignant tumors. Gonadotropin-releasing-hormone (GnRH) analogues, which suppress ovarian activity and reduce circulating levels of estrogen and progesterone, shrink fibroids and reduce associated uterine bleeding.

The current available treatment for uterine fibroids consists mainly of surgical intervention; while the pharmacological option is a hormonal treatment, which may help temporarily and has a limited effect, e.g. does not enable conception.

PEDF is a multifunctional factor endowed with neurotrophic, anti-angiogenic, anti-inflammatory and anti-oxidative properties which is ubiquitously expressed in the body. Despite significant expression in the reproductive system, there is only limited data about PEDF function in the ovary and uterus. Previous work has suggested using PEDF in the treatment of tumors due to its direct anti-tumorigenic and anti-angiogenic effect. However, the role of PEDF in protecting or treating uterine fibroids has never been disclosed.

Whilst reducing the present invention to practice, the present inventors have now uncovered that administration of PEDF affects the function of fibroids cells in-vitro and can attenuate growth of uterine fibroids in-vivo and thus suggest its use in the treatment of uterine fibroids.

As is illustrated herein below (Example 1 and FIGS. 1A-B, 2 and 3), the present inventors have found that rat fibroid ELT-3 cells express the PEDF receptors PNPLA2 and laminin-receptor; and once stimulated by recombinant PEDF (rPEDF) exhibit phosphorylation of ERK indicating activation of stress and apoptosis signaling and reduced expression of VEGF. Furthermore, the present inventors have established a uterine fibroid mouse model (Example 2, FIGS. 4A-C) and demonstrated that administration of rPEDF significantly reduces fibroid volume and, weight (Example 2, FIGS. 5A-C).

Thus, according to an aspect of the present invention there is provided a method of treating uterine fibroid in a subject in need thereof, the method comprising administering to the subject a therapeutically effective amount of pigment epithelium-derived factor (PEDF), thereby treating the uterine fibroid in the subject.

According to another aspect of the present invention there is provided a composition comprising pigment epithelium-derived factor (PEDF) for use in the treatment of uterine fibroid in a subject in need thereof.

According to yet another aspect of the present invention there is provided a use of pigment epithelium-derived factor (PEDF) in the manufacture of a medicament identified for the treatment of uterine fibroid in a subject in need thereof.

"Pigment epithelium-derived factor (PEDF)" is also known as serpin F1, EPC-1, cell proliferation inducing gene 35 protein and PIG35. According to a specific embodiment, the PEDF protein refers to the human protein, such as provided in the following GenBank Numbers M76979 (SEQ ID NO: 1), NM_002615 (SEQ ID NO: 2) or NP_002606 (SEQ ID NO: 3). PEDF, according to some embodiments of the present invention is functional in attenuating growth of uterine fibroids. The PEDF may also be functional in at least activating a PEDF receptor, interfering with VEGF signaling, inducing pro-survival, anti-angiogenic, anti-inflammatory, anti-tumorigenic and/or anti-oxidative signals. Methods of qualifying PEDF for use in accordance with the present invention are well known in the art (some are described in the Examples section e.g., effect on ERK phosphorylation, effect on VEGF expression in fibroid cells under hypoxia conditions, effect on fibroid volume, weight and/or proliferation in a uterine fibroid animal model, etc.).

The term PEDF refers to non-modified or modified PEDF. According to specific embodiments, the PEDF is a phosphorylated PEDF. PEDF is phosphorylated on 3 distinct sites Ser24 and Ser114 by casein kinase 2 (CK2) and on Ser227 by protein kinase A (PKA). Specifically, contemplated is the use of the triple phosphorylated PEDF. U.S. Publication No. US20080274967 teaches phosphorylation of PEDF using CK2 and PKA and is fully incorporated herein. PEDF can be recombinant (in a eukaryotic or prokaryotic expression systems including but not limited to, yeast, plant, insect, mammalian or bacterial expression systems), or purified as described in Yanagishe et al. 2006 J. Endocrinol. Metab. 91:2447-2450. Alternatively, PEDF is commercially available from e.g. Biovendor Inc.

The present invention also contemplates the use of PEDF peptides which retain the biological activity of full-length PEDF, i.e., treatment of uterine fibroids, such as those disclosed for example in U.S. Publication Nos. US20090069241 and US20120245097; and PCT Publication Nos. WO2014023007 and WO2013184986, each of which is herein incorporated by reference in its entirety.

As used herein a "PEDF Receptor", "PEDFR" or "PEDF-R" refers to a cell surface molecule which binds PEDF and initiates signal transduction such as via the FasL; CD95, Ras; Raf; Mekk1; Mek; Erk; JNK; IP3; Akt; IKK; NF-kappa-B; PLA2; and PPAR-γ pathways.

According to a specific embodiment, the PEDF receptor is an 80 kDa PEDF receptor, referred to as PEFD-R$^N$; PNPLA2, involved in PEDF neuroprotecting, pro-survival functions.

According to an additional or alternative embodiment, the PEDF receptor is a 60 kDa PEDF receptor, referred to as PEDF-R$^A$; laminin receptor, involved in PEDF pro-apoptotic, anti-angiogenic activities.

According to a specific embodiment, PEDF exerts its function through the 80 kDa PEDF receptor denoted PEFD-R$^N$ or PNPLA2.

The term "treating" refers to inhibiting or arresting the development of a pathology (disease, disorder, or condition) and/or causing the reduction, remission, or regression of a pathology. Those of skill in the art will understand that various methodologies and assays can be used to assess the development of a pathology, and similarly, various methodologies and assays may be used to assess the reduction, remission or regression of a pathology. In a certain embodiment treatment refers to prevention or preventing.

As used herein, the term "preventing" refers to keeping a disease, disorder or condition from occurring in a subject who may be at risk for the disease, but has not yet been diagnosed as having the disease. According to specific embodiments, the method or use further comprising administering the agent (i.e., which induces gonadal toxicity) or the uterine inducing toxicity agent e.g., tamoxifen to the subject.

As used herein, the phrase "subject in need thereof" refers to a mammalian female subject (e.g., human being) who is diagnosed with a uterine fibroid. In a specific embodiment, this term encompasses individuals who are at risk to develop uterine fibroid. The subject is typically at the reproductive age, however it can also be used in the treatment of a female subject under or above the reproductive age. Veterinary uses are also contemplated.

As used herein the term "reproductive age" refers to the age at which the subject is capable of sexual reproduction to enable fertilization either naturally or by intervention. According to specific embodiments, the subject is at a reproductive age.

According to specific embodiments, the subject is at the pre-menopausal period. In human menopause is defined as the state of an absence of menstrual periods for 12 months and in most women the post-menopausal period start between the ages of 45 and 55.

According to specific embodiments, the subject is 55 years of age or younger.

According to specific embodiments, the subject is 50 years of age or younger.

According to a specific embodiment, the subject is 35-55 years of age.

According to a specific embodiment, the subject is 35-50 years of age.

According to specific embodiments, the subject is not inflicted with cancer.

A uterine fibroid (also referred to as myoma or leiomyoma) is a benign non-cancerous neoplasm composed of disordered smooth-muscle cells buried in abundant quantities of extracellular matrix.

According to specific embodiments, the term "uterine fibroid" fibroid comprise a plurality of fibroids.

A subject having uterine fibroids typically presents the following symptoms which mostly depend on the location of the lesion and its size.

Major symptoms include abnormal gynecologic hemorrhage, heavy or painful periods, abdominal discomfort or bloating, painful defecation, back ache, urinary frequency or retention, and in some rare cases, anemia, infertility.

According to a specific embodiment, the subject does not suffer from fibroid associated infertility.

According to a specific embodiment, the subject is not diagnosed with infertility.

According to specific embodiments, the subject is fertile.

During pregnancy they may also be the cause of miscarriage, bleeding, premature labor, or interference with the position of the fetus.

According to specific embodiments, the uterine fibroid is an intramural fibroid.

As used herein, the term "intramural fibroid" refers to a fibroid located inside the uterine wall (i.e. the miometrium).

According to specific embodiments, the uterine fibroid is a subserosal fibroid.

As used herein, the term "subserosal fibroid" refers to a fibroid located in the outer layer of the uterus.

According to specific embodiments, the uterine fibroid is a cervical fibroid.

As used herein, the term "cervical fibroid" refers to fibroid located in the wall of the cervix.

According to a specific embodiment the uterine fibroid is not located in a submucosal position.

As used herein, the term "submucosal fibroid" refers to a fibroid located inside the uterine cavity, adjacent to the endometrium.

According to specific embodiments, PEDF can be used alone or in combination with other established or experimental therapeutic regimen to treat uterine fibroids, such as surgery and hormonal therapy (e.g. GnRH).

PEDF can be administered to the subject per se, or in a pharmaceutical composition where each or both are mixed with suitable carriers or excipients.

As used herein a "pharmaceutical composition" refers to a preparation of the active ingredient described herein with other chemical components such as physiologically suitable carriers and excipients. The purpose of a pharmaceutical composition is to facilitate administration of a compound to an organism.

Herein the term "active ingredient" refers to the PEDF accountable for the biological effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences", Mack Publishing Co., Easton, Pa., latest edition, which is incorporated herein by reference.

PEDF may be conjugated to an intrauterine device (IUD). Under a specific embodiment such a configuration allows slow release of PEDF (e.g., in situ).

Suitable routes of administration may, for example, include oral, rectal, transmucosal, especially transnasal, intestinal or parenteral delivery, including intramuscular, subcutaneous and intramedullary injections as well as intrathecal, direct intraventricular, intracardiac, e.g., into the right or left ventricular cavity, into the common coronary artery, intravenous, intraperitoneal, intranasal, or intraocular injections.

According to a specific embodiment, PEDF is administered (or formulated for administration) subcutaneously.

According to a specific embodiment, PEDF is administered (or formulated for administration) intramuscularly.

According to a specific embodiment, PEDF is administered (or formulated for administration) intravenously.

Alternately, one may administer the pharmaceutical composition in a local rather than systemic manner, for example, via injection of the pharmaceutical composition directly into a tissue region of a patient (e.g., gonads) such as by an imaging guided method (e.g., ultrasound).

Pharmaceutical compositions of some embodiments of the invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with some embodiments of the invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to some embodiments of the invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of some embodiments of the invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose.

As used herein, the phrase "therapeutically effective amount" refers to an amount of active ingredients (i.e., PEDF) effective to prevent, alleviate or ameliorate symptoms of a disorder (i.e., uterine fibroid) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals (as described in the Examples section which follows). The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide levels of the active ingredient that are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

Exemplary doses of PEDF are provided infra:
0.02-0.4 mg/kg/day, 0.162-0.32 mg/kg/day, 0.01-0.2 mg/kg/day, 0.1-0.4 mg/kg/day, 0.2-0.4 mg/kg/day or 0.05-0.1 mg/kg/day.

According to a specific embodiment, the PEDF is administered at a dosage range of 0.02-0.4 mg/kg/day.

According to another specific embodiment, the PEDF is administered at a dosage range of 0.162-0.32 mg/kg/day.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as is further detailed above.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

When reference is made to particular sequence listings, such reference is to be understood to also encompass sequences that substantially correspond to its complementary sequence as including minor sequence variations, resulting from, e.g., sequencing errors, cloning errors, or other alterations resulting in base substitution, base deletion or base addition, provided that the frequency of such variations is less than 1 in 50 nucleotides, alternatively, less than 1 in 100 nucleotides, alternatively, less than 1 in 200 nucleotides, alternatively, less than 1 in 500 nucleotides, alternatively, less than 1 in 1000 nucleotides, alternatively, less than 1 in 5,000 nucleotides, alternatively, less than 1 in 10,000 nucleotides.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

The Effect of PEDF on Uterine Fibroids In-Vitro

An in vitro cell culture system is used to test the effectiveness of recombinant PEDF (rPEDF) in attenuating proliferation of myometrial cells: rat ELT-3 cells; rodent primary cells; HuLM; UTSM; Primary Uterine Smooth Muscle Cells, Normal, Human (ATCC® PCS-460-011™) or others.

The tested effectiveness parameters are:
(A) Characterizing PEDF receptors;
(B) Monitoring rPEDF activity by evaluating its effect on the activity of P38, ERK and JNK, known PEDF substrates that mediate stress and apoptosis signaling; and
(C) Evaluating the effectiveness of rPEDF on cell proliferation and induction of apoptosis.
(D) Evaluating the effectiveness of rPEDF on reducing VEGF mRNA and protein level Materials and Methods RNA isolation, reverse transcription (RT) and polymerase chain reaction (PCR)—ELT-3 cells were cultured in 10% CS-FBS DF8 medium (as described by Howe S R, et al. The American journal of pathology. 1995; 146(6):1568-1579). Total RNA was isolated from ELT-3 cells using Trizol reagent (Invitrogen) according to manufacturer's instructions and quantified with the Nano-Drop spectrophotometer (ND-1000; Thermo Scientific). First-strand cDNA was produced by RT using high capacity cDNA reverse transcriptase kit (Applied biosystem (ABI), Carlsbad, Calif., USA) and random primers (ABI). For PCR: DNA was amplified by ReadyMix™ mixture (Sigma, St. Louis, Mo., USA), using specific primers for LR, PNPLA2 and GAPDH (control). PCR products (40× cycles, Tm=56) were separated by 1.5% agarose gel electrophoresis and visualized by ethidium bromide staining. The LH rat granulosa cell line was used as a positive control.

qPCR: Changes in the level of expression of mRNA were detected by SYBR green reagent (SYBR® Green PCR Master Mix, ABI, Carlsbad, Calif., USA; 40× cycles) along with 15 ng cDNA and specific primers, on a StepOnePlus Real-Time PCR System (Applied Biosystems, Foster City, Calif., USA).

PCR primers:

Western blot analysis—ELT-3 cells were homogenized in cold lysis buffer (20 mM HEPES, 150 mM NaCl and 0.2% Igepal; sigma) and centrifuged at 12,000 rpm, for 15 min, at 4° C.). Proteins were separated by sodium dodecyl sulfate polyacrylamide gel electrophoresis (SDS-PAGE; 10%; Bio-Rad, Israel). Separated proteins were transferred onto nitrocellulose membranes (Whatman GmbH, Germany) in a mini tank transfer unit (TE 22, Amersham, UK). Approximate molecular masses were etermined by comparison with the migration of pre-stained protein standards (Bio-Rad). Blots were blocked for 1 hour in TBST (10 mM Tris-HCl, pH=8.0, 150 mM NaCl, 0.05% Tween 20) containing 5% skim-milk (Alba, N.Y., USA) followed by an over-night incubation at 4° C. with primary antibodies: anti-PNPLA2 antibody (ABD66, Millipore, Temecula, Calif., USA), anti-Laminin receptor (LR) antibody (sc-20979; Santa Cruz Biotechnology, Santa Cruz, Calif. USA), anti-phospho ERK antibody and general ERK antibody (M9692 and M5670 respectively; Sigma, St. Louis, Mo., USA). Blots were washed three times in TBST and incubated for 1 hour at room temperature with horseradish peroxidase-conjugated secondary antibodies. Immunoreactive bands were visualized by enhanced chemiluminescence (ECL; Thermo Scientific, IL, USA) according to manufacturer's guidelines. Intensity of the protein bands was quantified by Image J sportswear (NIH).

Analysis of ERK phosphorylation—ELT-3 cells were incubated in a DF8 phenol free starvation medium (0.1% CS-FBS) for 16 hours and then stimulated with rPEDF (1 or 100 nM) or Tris (Control) for short periods of time (15, 30, 60 and 120 minutes). Cells were lysed and their proteins were western blotted as described above with anti-phospho ERK antibody, using general ERK as a loading control.

Analysis of VEGF mRNA expression—ELT-3 cells were incubated for 24 hours in a phenol free and insulin free DF8 medium, supplemented with CoCl2 (100 µM). Following incubation, the culture medium was replaced with fresh phenol free and insulin free starvation medium (0.1% CS-FBS) supplemented with fresh CoCl2 and rPEDF (20 nM) or Tris for additional 24 hours incubation. Changes in the level of VEGF mRNA were measured by qPCR analysis with specific primers and calibrated with HPRT as described above.

Results

The PEDF Receptor, PNPLA2, is Expressed in Uterine Fibroids Cells

Figure 1A:
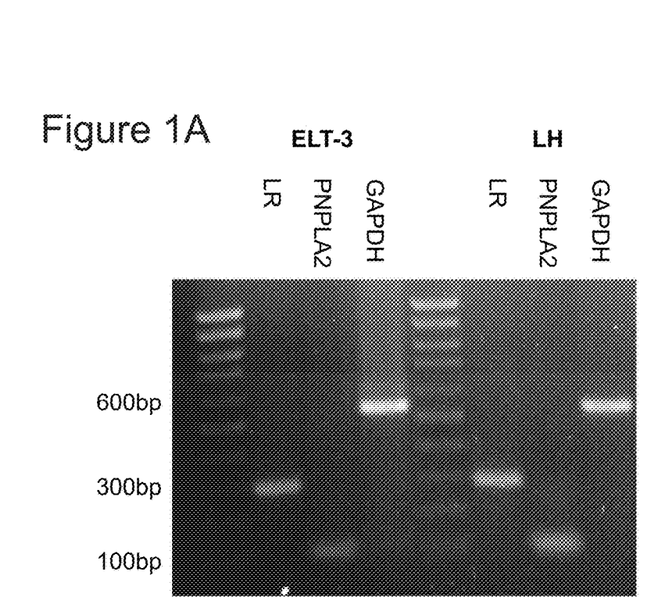
FIG. 1A is an auto radiograph of representative PCR analyses demonstrating mRNA expression of laminin receptor (LR) and PNPLA2 in ELT-3 cells and in LH rat granulose cell line (positive control). mRNA expression of GAPDH served as an internal control.
Figure 1B:
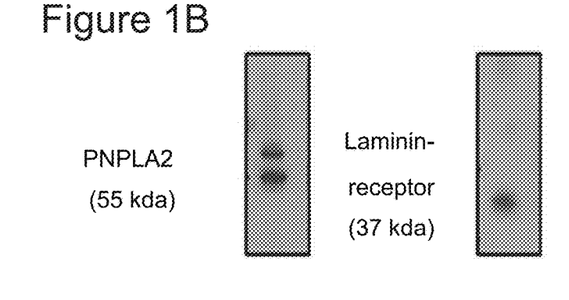
FIG. 1B is a representative Western blot photograph demonstrating protein levels of LR and PNPLA2 in ELT-3 cells using anti-LR and anti-PNPLA2 antibodies.

The present inventors have previously characterized PEDF activity in the ovary and found that both primary and cell lines of granulosa cells express PEDF receptors and that PEDF can directly modulate VEGF activity (Bar-Joseph H et al. Fertility and sterility. 2014; 102(3):891-898 e893). The PEDF receptors, Patatin-like phospholipase domain-containing protein 2 (PNPLA2), and Laminin receptor (LR) expression in Eker rat uterine leiomyoma ELT-3 cells, was evaluated at the protein and mRNA levels. As demonstrated in FIGS. 1A-B, ELT-3 cells express both PNPLA2 and LR, mRNA (FIG. 1A) and protein (FIG. 1B).

| PCR | GAPDH | | Foreword 5'GTGAAGGTCGGTGTGAACGG3' (SEQ ID NO: 4) |
| --- | --- | --- | --- |
| | | | Reverse 5'GTGATGGCATGGACTGTGGTC3' (SEQ ID NO: 5) |
| | PNPLA2 | | Foreword 5'TGTGGCCTCATTCCTCCTAC (SEQ ID NO: 6) |
| | | | Reverse 5'TGAGAATGGGGACACTGTGA(SEQ ID NO: 7) |
| | LR | | Foreword 5'TTGCCATTGAGAACCCTG (SEQ ID NO: 8) |
| | | | Reverse 5'TGGGATGGCAATGTCCAC (SEQ ID NO: 9) |
| qPCR | HPRT1 | Rat | Forward 5'CTCATGGACTGATTATGGACAGGA3' (SEQ ID NO: 10) |
| | | | Reverse 5'GCAGGTCAGCAAAGAACTTATAGCC3' (SEQ ID NO: 11) |
| | VEGF | Rat | Forward 5'CTATGCAGATCATGCGGATCA (SEQ ID NO: 12) |
| | | | Reverse 5'TATGCTGCAGGAAGCTCATCTC (SEQ ID NO: 13) |

Exogenous PEDF Activated ERK in Uterine Fibroids Cells

Figure 2:
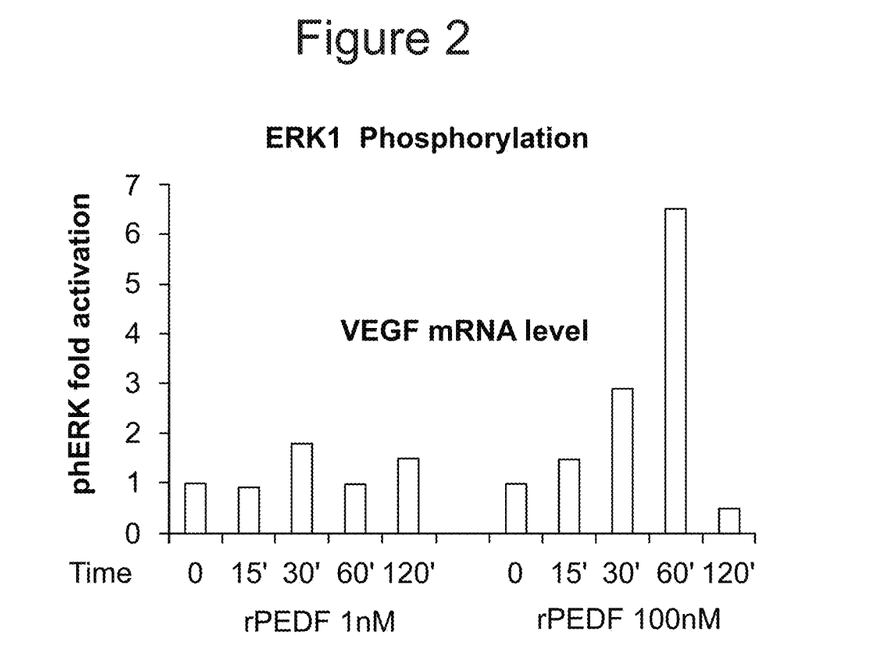

Having shown that ELT-3 cells express PEDF receptors, the ability of the PEDF receptors to transmit the recombinant PEDF (rPEDF) signal to ELT-3 cells was examined. To this end, serum-starved ELT-3 cells were stimulated with 1 or 100 nM rPEDF for various durations. The results indicated that stimulation with rPEDF induced activation of one of PEDF substrate, ERK as demonstrated by prolonged ERK phosphorylation, which starting 15 minutes following rPEDF treatment (FIG. 2).

Exogenous PEDF Modulated VEGF Expression Under Hypoxia Conditions in Uterine Fibroids Cells Hypoxia is one of the characteristics of uterine fibroids; therefore, the ability of rPEDF to modulate VEGF expression under hypoxia conditions using $CoCl_2$ was determine.

ELT-3 cells were incubated for 24 hours in a phenol free and insulin free DF8 medium, supplemented with CoCl2 (100 µM). Culture medium was then replaced with fresh phenol free and insulin free starvation medium (0.1% CS-FBS) supplemented with fresh CoCl2 and rPEDF (20 nM) or Tris for additional 24 hours incubation. Changes in the level of VEGF mRNA were measured by qPCR analysis with specific primers and calibrated with HPRT. Bars represent three independent experiments.

Figure 3:
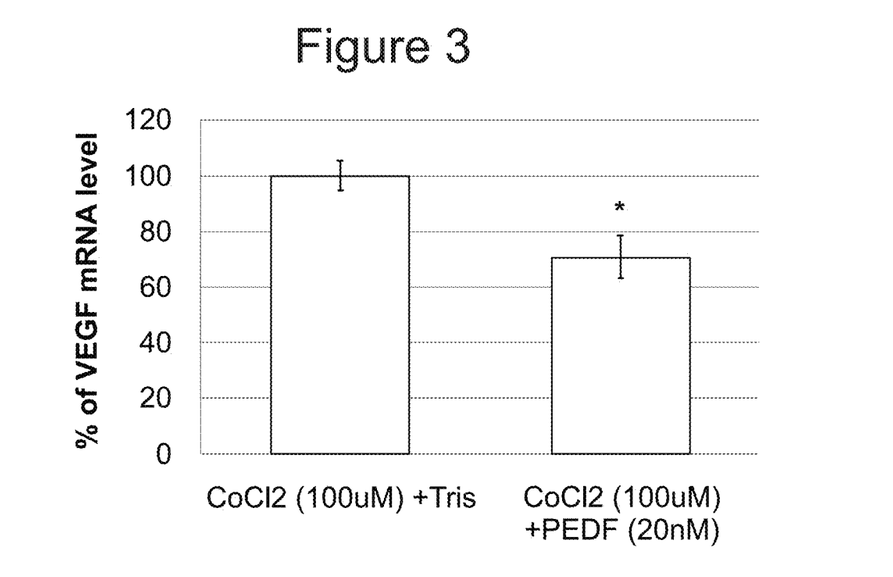
FIG. 3 is a graph demonstrating that PEDF reduces VEGF mRNA levels in ELT-3 cells under hypoxia conditions. ELT-3 cells were cultured in the presence of CoCl2 (100 μM) and then treated with rPEDF (20 nM) or Tris (Control). The y-axis represents VEGF mRNA levels relative to HPRT mRNA levels, as evaluated by qPCR. The Bars represent three independent experiments. The ratio between each treatment and control is plotted as Mean±SEM, (*$P<0.05$)—significantly different from control value.

The results indicated that stimulation with rPEDF significantly reduced VEGF mRNA level in hypoxia induced-ELT-3 cells (FIG. 3).

Taken together, rat fibroid cells express PEDF receptors; and once stimulated by rPEDF rat fibroid cells exhibit phosphorylation of ERK and reduced expression of VEGF.

Example 2

PEDF is Effective in Attenuating Growth of Unterine Fibroids in an Animal Model

Rodent uterine fibroids model: development of uterine fibroids is induced in Long Evans female rats or immune deficient SCID mice by injection of ELT-3 cells. The induced rodents are randomly divided into 2 groups to evaluate the effectiveness of recombinant PEDF (rPEDF) treatment: control (TRIS) and treatment (rPEDF) groups. Fibroids are excised, weighed and stored. Stored tumors and organs are subjected to pathologic evaluation and biochemical analysis.

Materials and Methods

Female SCID mice were synchronized with estrogen (2 µg on day −2) were injected SC to the flank with 1.5 million ELT-3 cells (100 µl) (day 0) (as described in Halder S K, et al. Reproductive sciences. 2014; 21(9):1108-1119; and Vaezy S, et al. American journal of obstetrics and gynecology. 2000; 183(1):6-11). Mice were treated with rPEDF (10 mg/kg) or Tris (control) once every 3 days from day 0 onwards. The fibroids were depicted and measured by ultrasound (US; Vevo 2100; Visual Sonics, Toronto, Canada) on days 8, 13, 22, 28 and 29). On day 29, mice were sacrificed; the fibroids were excised, weighed (mg) and measured by caliper ($mm^3$).

Results

Figures 4A, 4B:
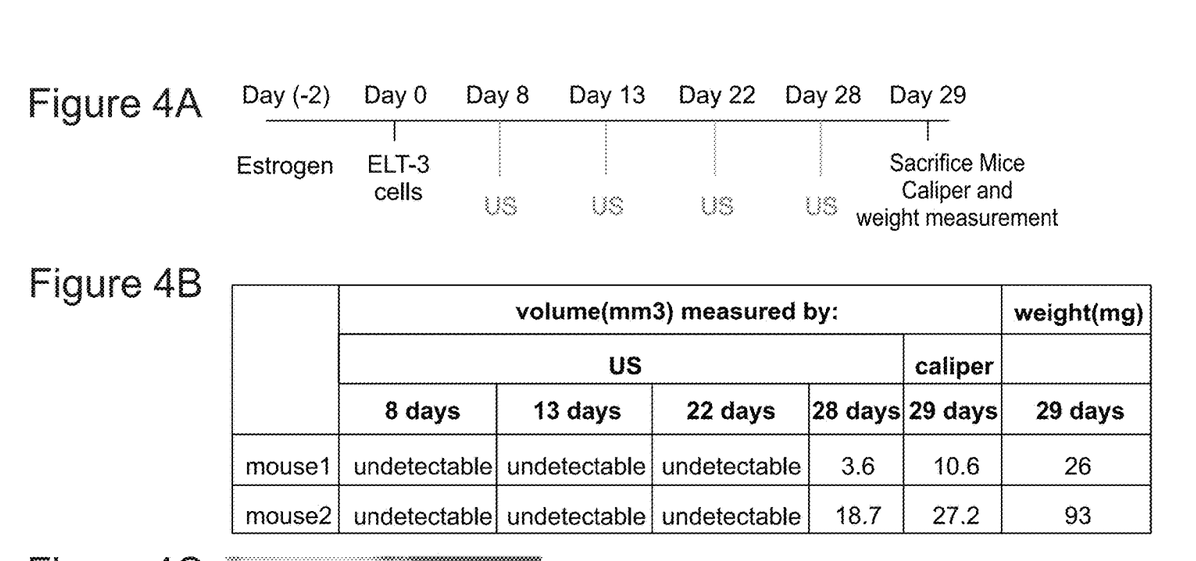
FIG. 4A is a schematic illustration of the experimental setting: Female SCID mice, synchronized with estrogen (day-2) were injected SC to the flank with ELT-3 cells (day 0). The fibroids were visualized and measured by ultrasound on days 8, 13, 22, 28 and 29. On day 29, mice were sacrificed and the fibroids were excised.
FIG. 4B demonstrates fibroids volume and weight evaluated in representative mice treated according to the setting depicted in FIG. 4A.
Figure 4C:
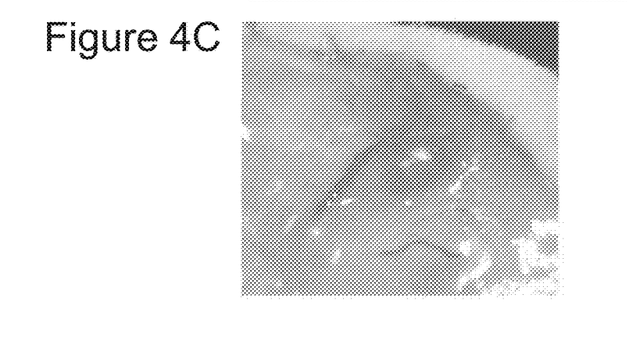
FIG. 4C is a picture of a fibroid obtained from a representative mouse treated according to the setting depicted in FIG. 4A.

In the first step an in vivo mice model for uterine fibroids was established. The established model was a female SCID mice synchronized with estrogen and injected with ELT-3 cells. Schematic representation of the established model and characterization of the uterine fibroids are shown in FIGS. 4A-C.

Figure 5A:
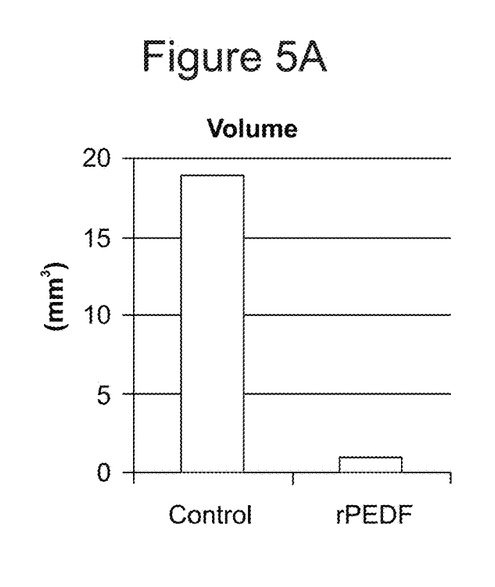
FIGS. 5A and 5B are graph bars demonstrating fibroid volume (FIG. 5A) and fibroid weight (FIG. 5B) in the treated mice.
Figure 5B:
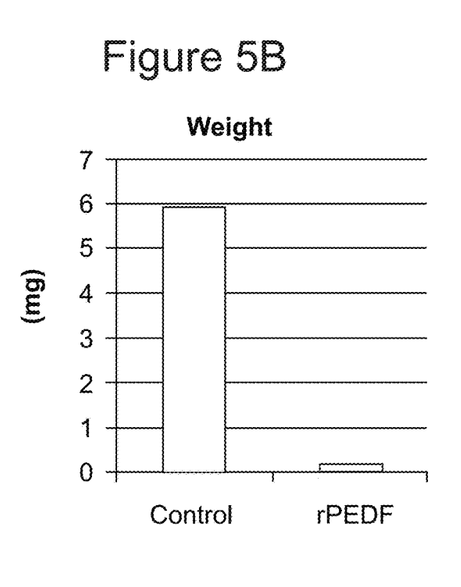
Figure 5C:
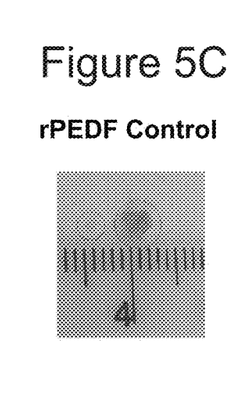
FIG. 5C is a picture demonstrating representative fibroids isolated from rPEDF-treated mouse as compared to Tris-treated (control) mouse.

To evaluate the therapeutic effect of rPEDF in vivo, mice with induced fibroids were treated with 10 mg/kg rPEDF or Tris (Control). The results indicated that uterine fibroids responded dramatically to the treatment (FIGS. 5A-C). Specifically, treatment with rPEDF decreased tumor volume (FIGS. 5A and 5C) and weight (FIG. 5B). It is suggested that the cell proliferation index is reduced by rPEDF compared to control, as can be determined by immunohistochemistry with anti-Ki67, PCNA or MCM2 antibody (see also for other markers Whitfield et al. 2006 Nat. Rev. 6:99-106).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A method of treating uterine fibroid in a subject in need thereof, the method comprising administering to the subject a therapeutically effective amount of pigment epithelium-derived factor (PEDF), thereby treating the uterine fibroid in the subject.

2. The method of claim 1, wherein said PEDF is attached to an intrauterine device.

3. The method of claim 1, wherein said uterine fibroid comprise a plurality of fibroids.

4. The method of claim 1, wherein said subject does not have malignant cancer.

5. The method of claim 1, wherein said subject does not have uterine fibroid associated infertility.

6. The method of claim 1, wherein said subject is not diagnosed with infertility.

7. The method of claim 1, wherein said subject is 50 years of age or younger.

8. The method of claim 1, wherein said subject is 55 years of age or younger.

9. The method of claim 1, wherein said subject is fertile.

10. The method of claim 1, wherein said subject is 35-50 years of age.

11. The method of claim 1, wherein said subject is 35-55 years of age.

12. The method of claim 1, wherein said uterine fibroid is an intramural fibroid.

13. The method of claim 1, wherein said uterine fibroid is a subserosal fibroid.

14. The method of claim 1, wherein said uterine fibroid is a cervical fibroid.

15. The method of claim 1, wherein said PEDF is formulated for local administration.

16. The method of claim 15, wherein said local administration is by injection into the uterine fibroid.

17. The method of claim 15, wherein said local administration is by an intrauteral device (IUD)-attached PEDF.

18. The method of claim 1, wherein said PEDF is formulated for systemic administration.

19. The method of claim 18, wherein said systemic administration is by subcutaneous or intramuscular administration.

* * * * *